United States Patent

Bowe, Jr. et al.

[11] Patent Number: 5,866,072
[45] Date of Patent: Feb. 2, 1999

[54] ANALYTICAL PYROLYSIS AUTOSAMPLER

[75] Inventors: Woodford A. Bowe, Jr., Rising Sun, Md.; Thomas P. Wampler, Newark, Del.

[73] Assignee: CDS Analytical, Inc., Oxford, Pa.

[21] Appl. No.: 806,322

[22] Filed: Feb. 26, 1997

Related U.S. Application Data

[60] Provisional application No. 60/012,311 Feb. 26, 1996.

[51] Int. Cl.[6] .......................... G01N 35/04; G01N 35/10; G01N 25/00
[52] U.S. Cl. ..................... 422/78; 73/863.11; 73/864.84; 422/64; 422/80
[58] Field of Search ........................... 73/863.11, 863.12, 73/863.71, 864.91, 864.21, 864.22, 864.24, 864.25, 864.84, 864.83, 864.81, 864.85, 23.41, 23.42, 61.55, 61.56, 61.59, 64.56; 422/64, 78, 80; 436/155, 174, 177, 179, 181

[56] References Cited

U.S. PATENT DOCUMENTS

| | | | |
|---|---|---|---|
| 3,475,950 | 11/1969 | Ferrin .................................. | 73/864.83 |
| 3,536,452 | 10/1970 | Norton et al. ...................... | 141/283 X |
| 3,731,539 | 5/1973 | Brittan et al. ....................... | 73/863.11 |
| 4,387,076 | 6/1983 | Cabrera et al. ................... | 73/864.82 X |
| 4,456,580 | 6/1984 | Kameda et al. ...................... | 422/78 X |
| 4,470,315 | 9/1984 | Ellgehausen et al. ............... | 73/863.12 |
| 4,476,733 | 10/1984 | Chlosta et al. ..................... | 73/863.91 |
| 4,600,827 | 7/1986 | Linwood et al. ...................... | 219/492 |
| 4,609,017 | 9/1986 | Coulter et al. .................. | 73/864.21 X |
| 4,693,867 | 9/1987 | Commormot et al. ............... | 422/78 X |
| 4,798,805 | 1/1989 | Issenmann .............................. | 436/157 |
| 5,236,353 | 8/1993 | Adani et al. ......................... | 422/78 X |
| 5,304,766 | 4/1994 | Baudet et al. ....................... | 422/78 X |
| 5,395,586 | 3/1995 | Hemzy et al. ....................... | 422/78 X |
| 5,578,268 | 11/1996 | Champseix et al. ................... | 422/63 |

*Primary Examiner*—Thomas P. Noland
*Attorney, Agent, or Firm*—Webb Ziesenheim Bruening Logsdon Orkin & Hanson, P.C.

[57] ABSTRACT

An apparatus for sequentially pyrolyzing a plurality of samples held in sample tubes comprises a substantially vertical passage through which tubes carrying the samples may be passed; an upper gas-tight valve for closing off the upper end of the passage; a lower gas-tight valve for holding a sample tube in the passage; a distribution valve directing purge gas and carrier gas to the top end of the passage and for passing pyrolyzed sample from the bottom of the passage to an analytical device; and an electrical heating element for heating the passage to temperatures at which a sample will be pyrolyzed.

8 Claims, 4 Drawing Sheets

ANALYTICAL PYROLYSIS AUTOSAMPLER

RELATED APPLICATION

This application is based upon Provisional Patent Application Ser. No. 60/012,311, filed Feb. 26, 1996.

BACKGROUND OF THE INVENTION

In the laboratory analysis of specimens by any of the well-known analytical methods including infrared spectroscopy or chromatography, it is desirable to automatically submit a large number of samples or specimens to the instrument performing the analysis without constant attendance. A number of types of automatic sampling systems (referred to generally as "autosamplers") are known and have embodiments for both solids and liquids.

Discrete autosamplers have a large number of sample compartments in which the individual samples or specimens are placed. Flow is diverted from each compartment in sequence to the analysis instrument. In the case of solids and some liquids which must be analyzed in the form of vapor, the sample is pyrolyzed (rapidly heated in the absence of reacting gases) to cause vaporization of the solid or liquid.

Another type of autosampler is the carousel/stacked type wherein samples are placed in holders (for example, bottles) and the contents of the holders are sequentially transferred to a common sampling chamber. This system usually requires a heated transfer line. This type of autosampler is not suitable for solids.

Another form of autosampler is a robot system that can emulate the manual one-by-one sample transfer.

The discrete autosamplers have a number of drawbacks: namely, many expensive probes (sample holding compartments) are required; a large multi-position valve for selecting probes is required which may suffer alignment problems; calibration numbers are required for repeatability; a very high electromechanical input/output count is required to switch power and sense lines for control of the autosampler; the dead volume is large; manual loading directly to probes can cause damage to the pyrolysis coils; a heated column isolation load/unload chamber is required; and a large number of isothermal zones are required.

The carousel/stacked autosamplers also have drawbacks: namely, numerous mechanical movement commands are required to transport the sample to the sampling chamber; a large dead volume in the stand-alone unit; a heated column isolation load chamber is required; complicated means (magnetic, vacuum or tactile) are required to move the sample in and out of the sample chambers; a count of samples as loaded is required; the sample chamber must reside close to the carousel or within the range of the x-, y-, z-axes of a robot loader; a heated transfer line is required between the pyrolysis chamber and the gas chromatography inlet; and precision positioning is required.

U.S. Pat. No. 4,798,805 discloses an apparatus for pyrolysis and analysis, one sample at a time. U.S. Pat. No. 3,536,452 discloses a system in which reactor tubes are fixed in a carousel so as the carousel is rotated each tube may be connected to an input reactant line. U.S. Pat. No. 4,476,733 discloses an autosampler for a gas chromatograph wherein sample containers are covered with a pierceable cover. The containers are advanced to a heater and then the cover of the containers is pierced to capture the heated specimen.

It is an advantage, according to this invention, to provide an autosampler for a pyrolysis device that overcomes the disadvantages of the prior art.

It is a further advantage that with the autosampler disclosed herein, results are repeatable due to the use of a single heating coil, no exposure of the analysis column to air during loading and unloading, and carrier flow which may be maintained at all times. Also, there is little or no carryover between samples due to the removal of the tube or container in which pyrolysis previously took place and a purge and clean cycle between runs. Also, the sample is purged to vent after the sample is loaded in the sample chamber providing an inert atmosphere prior to pyrolysis.

SUMMARY OF THE INVENTION

Briefly, according to this invention, there is provided an apparatus for sequentially pyrolyzing a plurality of samples held in independent sample tubes for analysis in an analytical device, such as a chromatograph. The apparatus comprises a substantially vertical passage through which tubes carrying the samples to be pyrolyzed may be passed. An upper gas-tight valve closes off the upper end of the passage in a closed position and passes the sample tube in the open position. A lower gas-tight valve holds the sample tube in the passage when in a closed position and passes the sample out of the vertical passage in the open position. The passage between the upper and lower gas-tight valves defines a pyrolysis chamber.

A gas distribution valve, which has inlets for receiving purge gas and carrier gas and in alternate positions directing purge gas or carrier gas to the top end of the pyrolysis chamber and for directing purge gas to a vent or carrier gas to the analytical device, is connected by conduits to the pyrolysis chamber near the upper gas-tight valve and to the pyrolysis chamber near the lower gas-tight valve. An electrical heating element for heating the pyrolysis chamber to a temperature at which the sample in a sample tube captured therein will be pyrolyzed is provided. A control system controls motors that actuate the upper and lower gas-tight valves, a motor that actuates the gas distribution valve and the heating element to sequentially move sample tubes into the pyrolysis chamber, pyrolyze the sample therein, and eject the sample tube after pyrolysis has taken place.

According to a preferred embodiment, a carousel is journaled for rotation above the vertical passage for carrying and dispensing sample tubes to the top of said passage. It is further preferred that the upper, lower and distribution valves are all mounted in a heater block so that they can be maintained at temperatures in excess of 150° C. to prevent condensation of the pyrolyzed sample. Typically, the heater block is enclosed in an insulated case. The sample tubes are sized to be carried by the carousel and to pass through the vertical passage. Preferably, the sample tubes are tapered at the exterior lower end and have a smaller opening at the lower end than at the top end. This facilitates the movement of the sample tubes through the valves and in and out of the vertical passage. It also facilitates retention of sample within the tubes. According to one embodiment, the sample tubes are packed with a glass wool or ceramic fibers to retain a liquid specimen within the tube by the forces of surface tension.

According to a preferred embodiment, the upper and lower valves are comprised of a valve body with a cylindrical interior having a substantially horizontal cylindrical axis. The inlet and outlet openings are aligned in a substantially vertical direction along a chord of the cylindrical interior. A rotating stopper is arranged to rotate on the substantially horizontal axis of the cylindrical interior. The stopper has a straight-through passage that can be brought into alignment with the inlet and outlet to permit a sample tube to pass therethrough.

According to a preferred embodiment, a ceramic, for example, quartz tube having an inner diameter greater than the outer diameter of the sample tubes, is aligned with and sealed to the outlet of the upper valve and the inlet of the lower valve. A furnace including the heating coil is positioned around the lower end of the ceramic tube.

BRIEF DESCRIPTION OF THE DRAWINGS

Further features and other objects and advantages of this invention will become clear from the following detailed description made with reference to the drawings in which.

DESCRIPTION OF THE PREFERRED EMBODIMENTS

The autosampler disclosed herein is an instrument which provides automatic multiple sampling for pyrolysis. Samples are loaded into quartz tubes which are placed vertically in a carousel. The quartz tubes are dropped sequentially into a pyrolysis chamber, pyrolyzed, then the spent tubes are dropped out of the bottom into a collection tray. Pyrolysis parameters of temperature, rate and time are set using a pyrolysis controller for controlling the current to the built-in coil heating the pyrolysis specimen or sample. The details of the pyrolysis controller are not a feature of this invention. Suitable controllers would include those described in U.S. Pat. No. 4,600,827 entitled "Dual-Powered Pyrolysis Probe Driving Circuit" and the most current model pyrolysis control sold by CDS Analytical, Inc., the assignee of this patent, under the trademark "Pyroprobe 2000". An autosampler or interface control sets the temperature of the pneumatics oven and facilitates communication among the sensors and motors of the autosampler, the pyrolysis controller and the analytical instrument, for example, gas chromatograph, to permit complete automation of the pyrolysis and gas chromatography process with remote start of the gas chromatograph and wait for ready intelligence.

Figure 1:
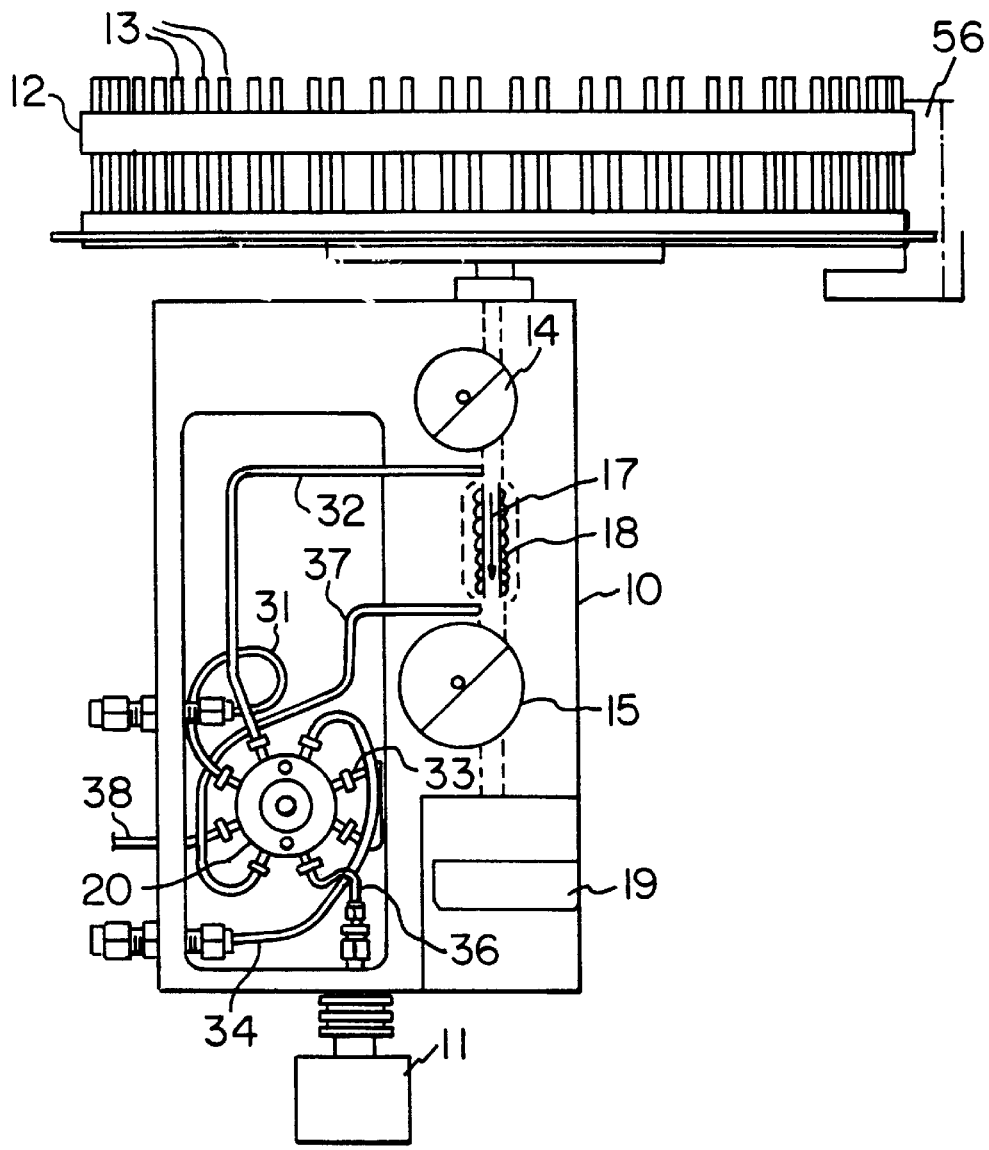
FIG. 1 is a schematic front view of an autosampler with the pneumatics oven cover removed, according to this invention.

Referring now to FIG. 1, the autosampler is shown schematically at 10 connected to the injection port 11 of a gas chromatograph which may be the existing split/splitless or packed injection port. The carousel 12 carries a plurality of sample tubes 13. When the carousel 12 rotates to align a sample tube with the inlet to the autosampler, the sample tube may drop into the sample tube guide 16 of the autosampler. The autosampler has an upper gas-tight valve 14 and a lower gas-tight valve 15. A pyrolysis chamber 17 is positioned between the outlet of the upper gas-tight valve and the inlet to the lower gas-tight valve with ends sealed to the outlet of the upper valve and the inlet of the lower valve. The ceramic tube defining the pyrolysis chamber 17 is surrounded by heating coil 18. The electrical current to the heating coil is controlled by the pyrolysis controller (not shown). A spent tube tray 19 is positioned to collect sample tubes after they are ejected from the vertical passage.

A gas distribution valve 20 controls the flow of carrier gas and purge gas to the pyrolysis chamber 17 and the flow away from the chamber to either the vent or the inlet to the gas chromatograph. The plumbing surrounding the distribution valve is best understood by reference to FIG. 2. The distribution valve has eight ports 21–28. Each odd-numbered port can be connected to either one or the other even-numbered port adjacent to it. Port 21 is connected through conduit 31 to valve 30 to which purge gas is supplied. Port 22 is connected by conduit 32 to the upper end of pyrolysis chamber 17. Conduit 32 is in communication with the upper end of the pyrolysis chamber no matter what the position of upper gas-tight valve 14. Port 23 is connected by conduit 33 to port 25. Port 24 is connected by conduit 34 with valve 29 through which carrier gas is supplied. Port 26 is connected by conduit 36 to the gas chromatograph, for example, through a universal needle adaptor. Port 27 is connected by conduit 37 to the lower end of the pyrolysis chamber. Port 28 is connected by conduit 38 to a vent to the atmosphere.

Figure 2:
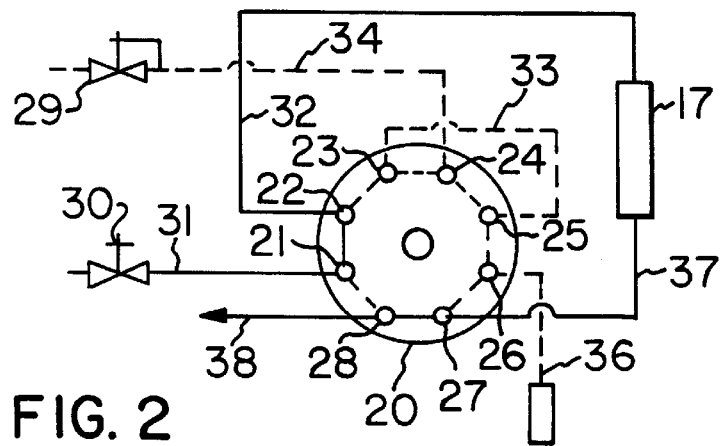
FIG. 2 is a diagram illustrating the pneumatic flow controlled by the distribution valve.

Thus, when the distribution valve is in the de-energized position as shown in FIG. 2, carrier gas is passed directly through ports 23, 24, 25 and 26 directly to the gas chromatograph. Also, sample purge gas is passed through ports 21, 22, 27 and 28 through the pyrolysis chamber to vent. In the energized position of the distribution valve, carrier gas is passed through ports 23, 22, 27 and 26 to the gas chromatograph after first flushing the pyrolysis chamber. Also, purge gas is directed to the vent through ports 21 and 28 if the valve 30 is not closed.

Figure 3:
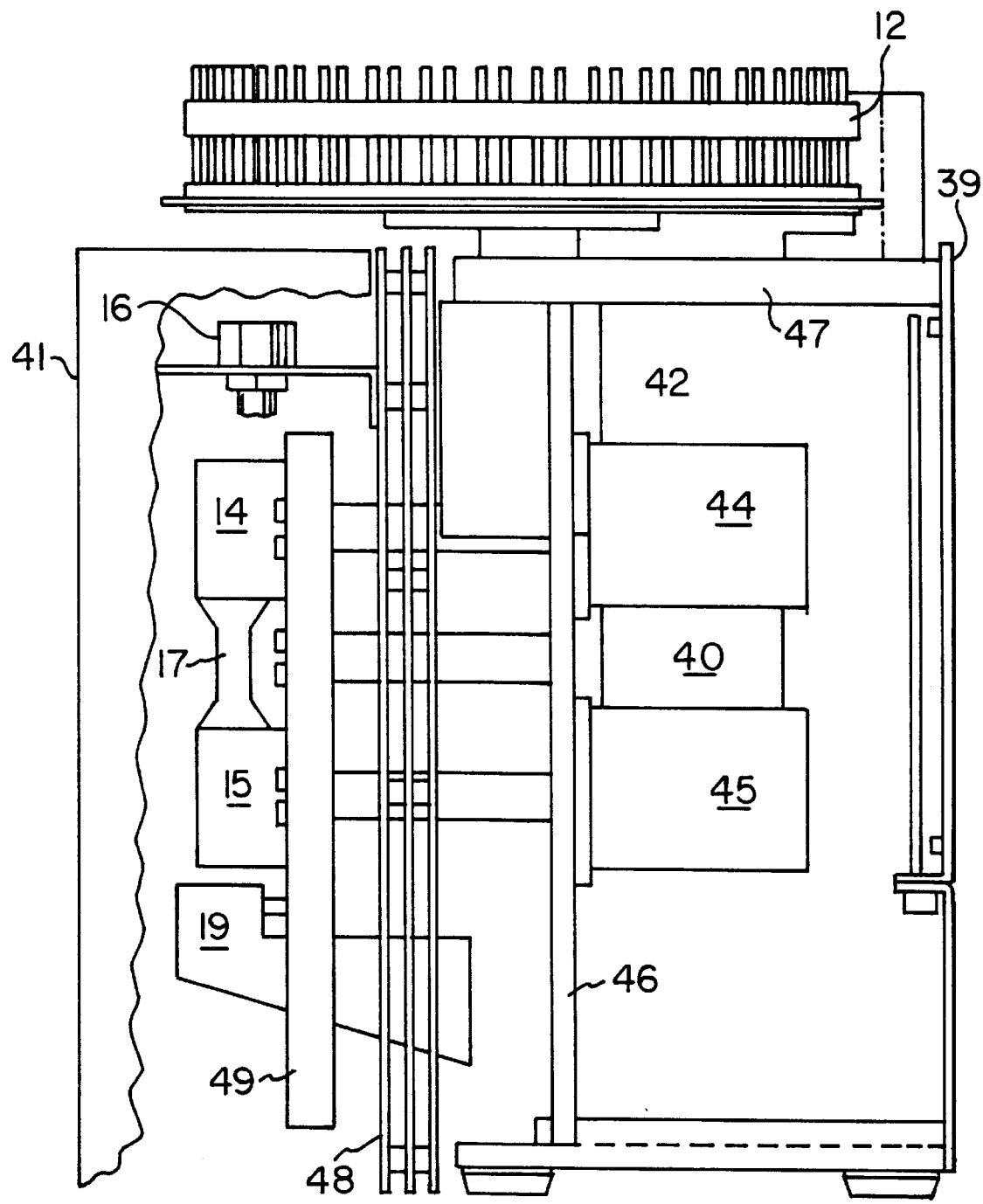
FIG. 3 is an exploded side view of an autosampler, according to this invention, with a side panel removed and the pneumatics oven cover broken away, illustrating the positioning of the motors for actuating the carousel, the upper and lower gas-tight valves and the distribution valve.

Referring now to FIG. 3, the autosampler housing is divided into two compartments: motor compartment 39 and pneumatics oven defined by cover 41. Compartment 39 houses the valve motors, carousel motor and certain electronics. The motor compartment has a vertical motor mounting plate 46 and a horizontal mounting plate 47. The motor 42 for rotating the carousel is mounted to the horizontal mounting plate 47. Motor 44 for energizing the upper gas-tight valve 14, motor 45 for energizing the lower gas-tight valve 15 and motor 40 for energizing the distribution valve 20 are mounted on vertical motor mounting plate 46. A radiant heat insulating shield 48 is positioned between the motor compartment and the contents of the pneumatics oven which comprise heater block 49 in which the upper and lower gas-tight valves and distribution valve are mounted. The heater block 49 has a resistance coil (not shown) associated therewith for controlling the temperature thereof. A movable insulating cover 41 and sample guide enclose the heater block and the valves mounted therein. When the insulated cover encloses the heater block, it defines the enclosure for the pneumatics oven.

Figure 4:
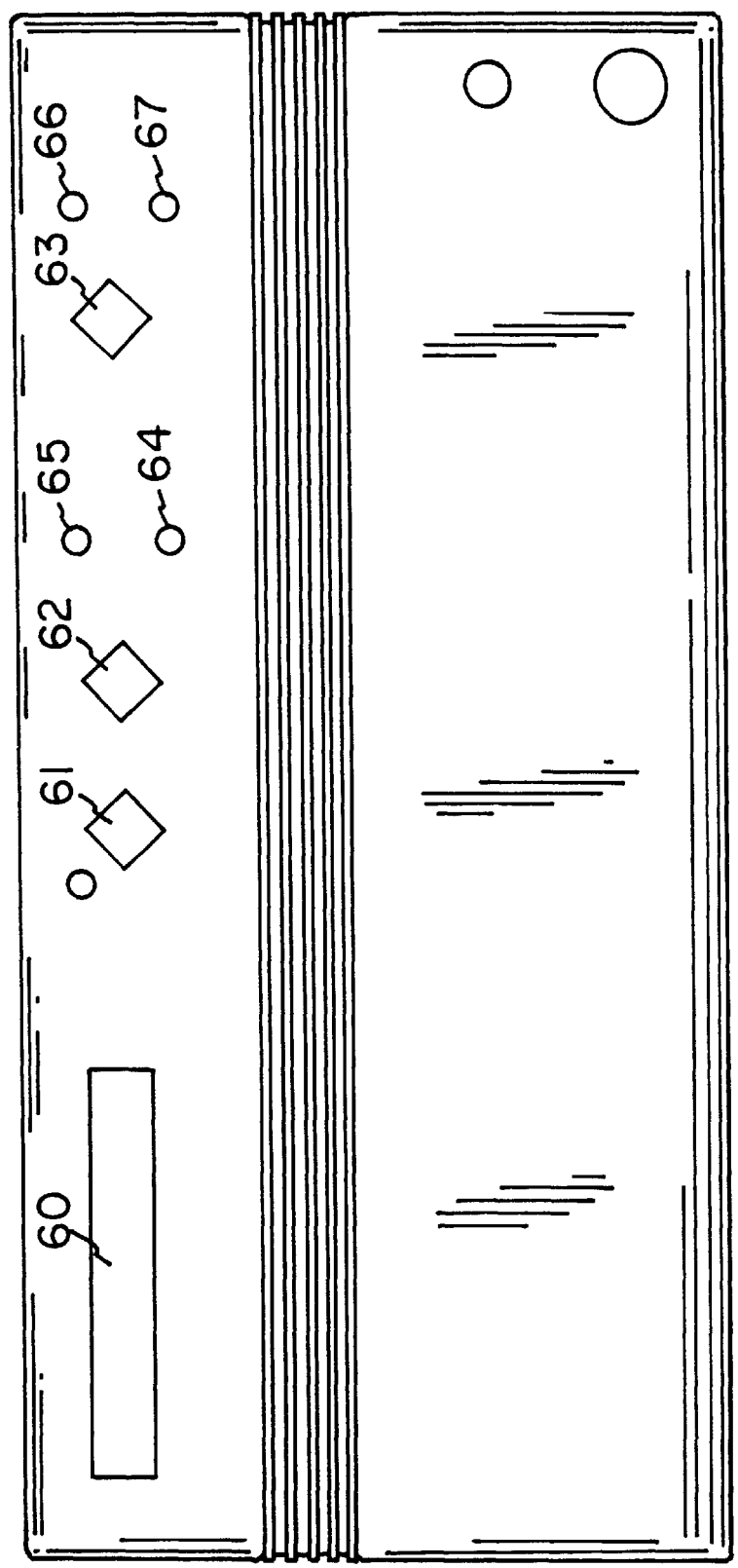
FIG. 4 is a front panel of a controller for controlling the autosampler according to this invention.

Referring now to FIG. 4, there is shown the front panel of an interface or autosampler controller. The front panel has a display for displaying a series of alphanumeric characters. The front panel has three switches, a start switch 61, an advance switch 62 and a clean mode switch 63. The front panel has probe and gas chromatograph ready lights 65 and 64, respectively, and clean mode lights 66 and 67, respectively, displaying vent or gas chromatograph modes.

The message center 60 (alphanumeric display) of the autosampler controller indicates the status of the instrument as well as corrective action when required. When idle, the autosampler will display a ready message, indicating that it is ready for operation. During the course of a run, the message center displays the current status of the instrument in the following sequence: SAMPLE LOADING; SAMPLE PURGE; SAMPLE ON-LINE; ON-LINE EQUIL; PYROLYZING; POST PYRO DELAY; CHECKING DISCHARGE; POST CLEAN (vent); WAITING FOR GC. After the GC ready is sensed, the message center will indicate ADVANCING if another sample is to be run, or HOMING if all samples have been run and the carousel is returning to the home position.

Figure 5:
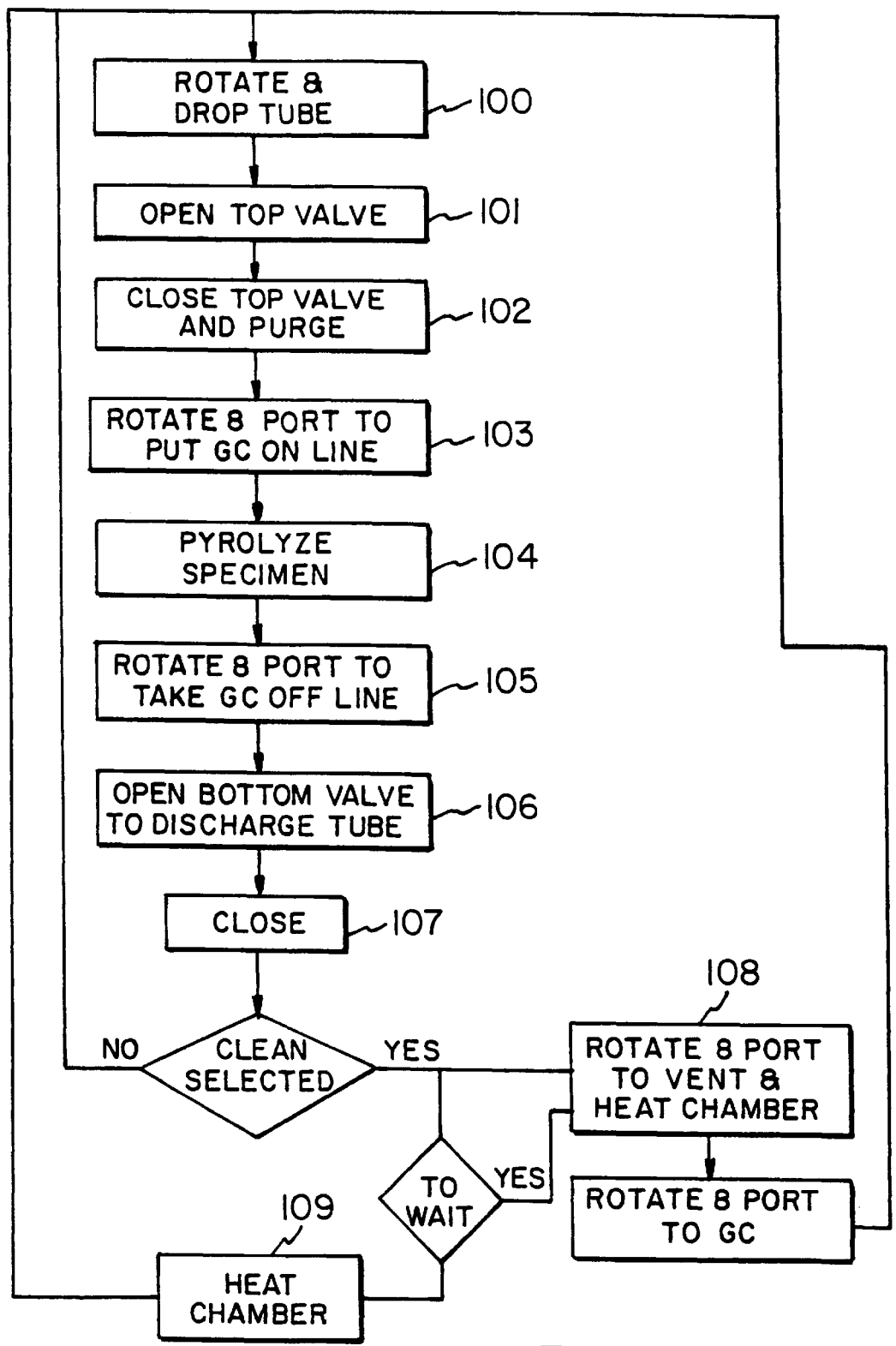
FIG. 5 is a flow diagram for a control program for processing sample tubes through the autosampler and the pyrolysis chamber.

Referring to FIG. 5, in the automatic mode, the autosampler functions as follows: the carousel rotates to drop in the first sample tube 100; the upper gas-tight valve 14 opens, and the sample tube drops into the pyrolysis chamber 101; valve 14 closes, and the chamber is purged to vent to remove air before pyrolysis 102; the eight-port distribution valve 20 is energized to put the pyrolysis chamber on-line with the GC injection port, and a delay time permits reestablishment of GC flow and pressure 103; the sample is pyrolyzed, using the platinum coil surrounding the pyrolysis chamber. A start signal is sent to the GC, and a post pyrolysis delay permits sweeping the pyrolysate onto the GC column 104; the pyrolysis chamber is taken off-line from the GC by deenergizing the distribution valve 105; the sample discharge valve 15 is opened, permitting the spent tube to drop into the collection tray 106; the discharge valve is closed at 107, and if selected, the pyrolysis chamber is cleaned to vent 108 by heating the platinum coil a second time. Alternately, the pyrolysis chamber can be cleaned to the GC 109. After the above process, the autosampler waits for a "GC Ready" signal before advancing the carousel to the next sample.

The pyrolysis autosampler may also be used in a manual mode to analyze one sample, without the carousel. In this mode, a sample is placed into the loading chute manually, and when the autosampler is started, all of the above steps occur one time only. At the completion of the pyrolysis run, the tube is discharged, and the autosampler is again in the ready mode.

Referring to FIG. 5, the autosampler control panel is simple because most of the information needed for operation is supplied by amplified reflective photomicrosensors. Five sensors are used to provide various pieces of information concerning the mode, status and position of the autosampler. Specifically, these are as follows: a "carousel in place" sensor, which tells the autosampler whether or not a sample tray has been loaded; if the carousel is in place, the autosampler proceeds in the automatic mode, and if it is not, the autosampler is in the manual mode, for the analysis of one sample tube; a "home" sensor, which guarantees that the carousel is in the proper orientation at the beginning of a run; a "position" sensor which tells the autosampler which sample location is being run, and enables the display of the sample position on the message center screen; a tube sensor which counts and locates each sample tube in the carousel; and a tube discharge sensor which checks to see that the spent tube has dropped out of the pyrolysis chamber before another is allowed in.

The sample tube sensor recognizes both the presence and position of the sample tubes, so there is no need to load the carousel in any particular way. As the carousel rotates, the sensor tells the autosampler which positions have samples in them, and the carousel stops only at those positions, skipping any empty slots.

Depending on the information from the sensors, messages may be displayed on the message center indicating appropriate action. When the tray is first installed, the message "rotate tray to home" will indicate that the carousel is not in the home position. When this is corrected, the autosampler will automatically continue the run. If the tube discharge sensor does not register that the tube has dropped out of the pyrolysis chamber, the message "no discharge" is shown and the unit will not advance until the operator guarantees that the sample path is clear.

Pressing the Start/Stop button 61 (FIG. 4) once initiates the run. If no sample carousel is in place, the unit goes through one sequence for a manual run. If the carousel is in place and properly homed, the run sequence begins. If the carousel is not homed, the "rotate tray to home" message is displayed and the operator must manually rotate the tray until it is properly homed, at which time the carousel motor will automatically take over and begin the run. If the Start/Stop button is pressed again, the run stops and the tray returns to the home position.

The advance button 62 is used to advance the autosampler to the next step if it has paused or to abort a run. For example, if the tube discharge sensor does not register that the tube has dropped, the unit will display "no discharge" and wait for corrective action. After the user has made sure that the sample path is clear, pressing advance moves the unit to the next step, resuming the sequence. Further, a sample may be manually skipped by pressing the advance. If the sample has dropped into the pyrolysis zone, but not yet pyrolyzed, pressing advance drops the unpyrolyzed sample out of the chamber, does not start the GC and moves to the next sample tube.

After pyrolysis, the autosampler has three options for cleaning the pyrolysis chamber selected by the clean button 63. The chamber may be cleaned to vent or it may be cleaned to the GC on the next run as a check on the system contamination or the clean step may be skipped altogether. Pressing the clean button lights either "vent", meaning that the system will be cleaned to vent immediately after the tube is discharged, "GC", meaning that the system will conduct a complete clean to GC blank run, including running the GC, or neither, meaning that the clean function is not being used.

There are four lights on the control panel of the autosampler, two next to the clean button, as described above, 66 and 67. The two lights between the advance and clean buttons are pyrolysis controller ready 65 and GC ready 64 indicators. When illuminated, the corresponding device is ready, so the probe light should be on at any time when the coil is not actually firing (for pyrolysis or cleaning) and the GC light should be on only when the GC is not currently in a run or cooling down.

Samples for analysis using the autosampler must be placed into a quartz tube and positioned vertically in the carousel (see FIG. 1). The autosampler quartz tubes are fire-polished on one end, and it is important that the fire-polished end is placed down to prevent tubes from jamming in the loading valve. Samples may be positioned in the tube with either quartz wool or by using a quartz placement rod, or a combination. Samples may be placed near the top of the tube since the top end of the tube is within the pyrolysis coil during heating. Attention should be paid to samples which will melt either at the pneumatics oven temperature or during the early stages of pyrolysis heating, since the tube is positioned vertically during pyrolysis and the melted sample will run down the tube. A generous plug of quartz wool below the sample and placement at the top portion of the tube will help maximize pyrolysis. In all cases, it must be remembered that the sample being pyrolyzed goes directly to the column inlet and, therefore, the sample size must be compatible with the gas chromatograph. In general, samples should be smaller than 1 mg, with sizes of 10 to 100 μg being preferred.

The autosampler carousel fits onto the top of the autosampler over the carousel hub. The carousel has a bottom plate that rotates relative to the portion of the carousel into which the sample tubes are stacked. The bottom plate has a single hole that permits the sample tubes to drop through when they are aligned with the hole. The carousel has a small hole near the hub for a tall alignment pin, a hole on the bottom for the short alignment pin and a notch for the sample tube sensor. When the carousel is properly aligned, the hole in the bottom plate aligns with the sample tube guide 16. The carousel should be placed over the tall alignment pin and hub first, then rotated so that the sensor notch lines up with the sensor. As the carousel slides down the hub, with the notch going over the sensor, the short alignment pin and corresponding hole should engage and the carousel should be in the "home" position. If it is not, a message will appear in the message center when the start button is pressed.

Once the carousel is loaded and in position on the autosampler and the pyrolysis controller is programmed with the desired pyrolysis, clean and interface (pneumatics oven) setpoints, the run is initiated by pressing the "start" button. If the GC is not ready, the message center will display "waiting for GC". If the GC is ready, the autosampler will begin its run. If the carousel is not in the "home" position, "rotate tray to home" will be displayed after the start button is pressed. If this is displayed, the operator slowly rotates the tray to the home position (notch directly at sensor). As soon as the unit senses that the carousel is in the home position, the carousel motor will engage and drive it clockwise, then reverse to insure homing, then the carousel is rotated to the first sample position, and the run begins.

Having thus described our invention with the detail and particularity required by the Patent Laws, what is desired protected by Letters Patent is set forth in the following claims.

What is claimed is:

1. Apparatus for sequentially pyrolyzing a plurality of samples held in sample tubes for analysis in an analytical device comprising:

means for defining a substantially vertical passage through which the tubes carrying the samples may be passed;

an upper gas-tight valve for closing off the upper end of the passage in a closed position and passing a sample tube in an open position;

a lower gas-tight valve for holding the sample tube in the passage when in a closed position and for passing the sample tube in an open position;

a distribution valve having inlets for receiving purge gas and carrier gas for, in alternate positions, directing purge gas and carrier gas to the top end of the passage and for passing pyrolyzed sample from the bottom of the passage to said analytical device;

an electrical heating element for heating the passage to temperatures at which the sample in the sample tube positioned therein will be pyrolyzed; and means to control the upper, lower, and distribution valves and the heating element to sequentially move the sample tube into the vertical passage, pyrolyze the sample therein and eject the sample tube after pyrolysis has taken place.

2. The apparatus according to claim 1, further comprising a carousel journaled for rotation above the vertical passage and for carrying and dispensing sample tubes to the top of said passage.

3. The apparatus according to claim 2, further comprising a plurality of sample tubes sized to be carried by the carousel and passed through the vertical passage.

4. The apparatus according to claim 3, in which each of the sample tubes is tapered at an exterior lower end thereof and has a smaller opening at the lower end than at a top end thereof.

5. The apparatus according to claim 1, wherein the upper, lower and distribution valves are mounted in a heater block so that they can be maintained at temperatures in excess of 150° C.

6. The apparatus according to claim 5, wherein the valves and the heater block are enclosed in an insulated case.

7. The apparatus according to claim 1, wherein the upper and lower valves are comprised of a valve body with a cylindrical interior having a substantially horizontal cylindrical axis, inlet and outlet openings aligned in the substantially vertical direction along a chord of the cylindrical interior, a rotating stopper arranged to rotate on the substantially horizontal axis of the cylindrical interior, said stopper having a straight-through passage that can be brought into alignment with the inlet and outlet to permit the sample tube to pass therethrough.

8. The apparatus according to claim 1, wherein a ceramic tube having an inner diameter greater than the outer diameter of the sample tube is aligned with and sealed to an outlet of the upper valve and an inlet of the lower valve and said apparatus further comprising a heating coil positioned around a lower end of the ceramic tube.

* * * * *